(12) United States Patent
Truschel et al.

(10) Patent No.: US 10,518,050 B2
(45) Date of Patent: Dec. 31, 2019

(54) SYNCHRONOUS AIRWAY PRESSURE RELEASE VENTILATION

(71) Applicant: KONINKLIJKE PHILIPS N.V., Eindhoven (NL)

(72) Inventors: William Anthony Truschel, Oakmont, PA (US); John Seymour, New Kensington, PA (US)

(73) Assignee: Koninklijke Philips N.V., Eindhoven (NL)

( * ) Notice: Subject to any disclaimer, the term of this patent is extended or adjusted under 35 U.S.C. 154(b) by 826 days.

(21) Appl. No.: 14/897,019

(22) PCT Filed: Jun. 5, 2014

(86) PCT No.: PCT/IB2014/061965
§ 371 (c)(1),
(2) Date: Dec. 9, 2015

(87) PCT Pub. No.: WO2014/199264
PCT Pub. Date: Dec. 18, 2014

(65) Prior Publication Data
US 2016/0151594 A1 Jun. 2, 2016

Related U.S. Application Data

(60) Provisional application No. 61/833,552, filed on Jun. 11, 2013.

(51) Int. Cl.
*A61M 16/00* (2006.01)
(52) U.S. Cl.
CPC ...... *A61M 16/0069* (2014.02); *A61M 16/024* (2017.08); *A61M 2016/0015* (2013.01);
(Continued)

(58) Field of Classification Search
CPC .............. A61M 16/00; A61M 16/0003; A61M 16/0006; A61M 16/0009; A61M 16/0057;
(Continued)

(56) References Cited

U.S. PATENT DOCUMENTS

| 4,773,411 A | 9/1988 | Downs |
| 5,513,631 A | 5/1996 | McWilliams |

(Continued)

FOREIGN PATENT DOCUMENTS

| WO | WO9945989 A1 | 9/1999 |
| WO | WO2011057362 A1 | 5/2011 |
| WO | WO2011070472 A1 | 6/2011 |

*Primary Examiner* — Jospeh D. Boecker
(74) *Attorney, Agent, or Firm* — Michael W. Haas (57) ABSTRACT

A pressure control ventilation system (10) configured to provide airway release ventilation synchronous with a breathing subject that includes a pressure generator (12) configured to generate pressurized flow of breathable gas to a subject, one or more sensors (28) configured to generate output signals conveying information related to one or more gas parameters of the pressurized flow, one or more processors (14) configured to execute computer modules comprising: a synchronization module (16) configured to detect inspiratory (39, 45) and expiratory (40, 44, 59) flow phases of the subject based at least on the signals; an interval module (18) configured to define time intervals (54, 60); a control module (20) configured to control the generator to deliver flow fluctuating between a first pressure range (48) to maintain adequate lung volume and a second pressure range (50) to facilitate C02 exhalation, the control including: delivering the flow in the first range at the beginning (56) of a first time interval (54); adjusting the flow from the first to the second range responsive to a detection of a start (42) of a first expiratory flow phase (40) in the first time interval; maintaining the flow at the second range over the first expiratory phase; and maintaining the flow at the first range (Continued)

over a second expiratory phase (44) starting in the first time interval and following the first expiratory phase.

15 Claims, 4 Drawing Sheets

(52) U.S. Cl.
CPC ............... *A61M 2016/0039* (2013.01); *A61M 2205/3365* (2013.01)

(58) Field of Classification Search
CPC .......... A61M 16/0066; A61M 16/0069; A61M 16/022; A61M 16/024; A61M 2016/0015; A61M 2016/0018; A61M 2016/003; A61M 2016/0033; A61M 2016/0039; A61M 2205/3334; A61M 2205/3365
See application file for complete search history.

(56) References Cited

U.S. PATENT DOCUMENTS

| | | | |
|---|---|---|---|
| 6,213,119 B1* | 4/2001 | Brydon | ............... A61M 16/024 128/204.18 |
| 2003/0045807 A1* | 3/2003 | Daniels, II | ............. A61B 5/083 600/538 |
| 2003/0111078 A1* | 6/2003 | Habashi | ................ A61M 16/00 128/204.18 |
| 2006/0000475 A1* | 1/2006 | Matthews | ......... A61M 16/0051 128/204.21 |
| 2006/0011195 A1 | 1/2006 | Zarychta | |
| 2006/0124130 A1 | 6/2006 | Bonassa | |
| 2007/0215146 A1* | 9/2007 | Douglas | ................ A61M 16/00 128/200.24 |
| 2008/0295839 A1* | 12/2008 | Habashi | ............ A61M 16/0051 128/204.22 |
| 2008/0295840 A1 | 12/2008 | Glaw | |
| 2009/0095297 A1 | 4/2009 | Hallett | |
| 2011/0023880 A1 | 2/2011 | Thiessen | |
| 2011/0197887 A1* | 8/2011 | Truschel | ........... A61M 16/0051 128/204.23 |
| 2011/0240025 A1* | 10/2011 | Mechlenburg | ...... A61M 16/026 128/204.21 |
| 2012/0055484 A1 | 3/2012 | Shaw | |
| 2012/0234324 A1* | 9/2012 | Orr | ....................... A61M 16/00 128/204.22 |

* cited by examiner

SYNCHRONOUS AIRWAY PRESSURE RELEASE VENTILATION

This patent application claims the priority benefit under 35 U.S.C. § 371 of international patent application no. PCT/IB2014/061965, filed Jun. 5, 2014, which claims the priority benefit under 35 U.S.C. § 119(e) of U.S. Provisional Application No. 61/833,552 filed on Jun. 11, 2013, the contents of which are herein incorporated by reference.

BACKGROUND OF THE INVENTION

1. Field of the Invention

The present disclosure pertains to systems and methods for pressure control ventilation, and, in particular, to provide airway pressure release ventilation which is synchronous to a patient's breathing pattern.

2. Description of the Related Art

Airway pressure release ventilation is a method of bilevel pressure ventilation that produces a severe inverse ratio to periodically eliminate carbon dioxide from the airway of a subject, while maintaining a high positive airway pressure or Mean Airway Pressure for alveolar recruitment. It was described by Stocks and Downs in 1987 and is indicated to treat acute lung injury along with other respiratory complications.

SUMMARY OF THE INVENTION

Accordingly, one or more aspects of the present disclosure relate to a pressure control ventilation system configured to provide airway pressure release ventilation synchronous with a breathing subject, the pressure support system comprising a pressure generator configured to generate pressurized flow of breathable gas, one or more sensors configured to generate output signals conveying information related to one or more gas parameters of the pressurized flow of breathable gas, and one or more processors configured to execute computer program modules.

The computer program modules comprise a synchronization module configured to detect inspiratory and expiratory flow phases of the breathing subject, including detecting starts and ends of the inspiratory and expiratory flow phases of the breathing subject, the detection based in part on the output signals of the one or more sensors, an interval module configured to define time intervals, the time intervals including beginning times and end times, and a control module configured to control the pressure generator to deliver pressurized flow of breathable gas with a pressure that fluctuates between first and second pressure ranges such that at the first higher pressure range the lungs of the subject are supported by the pressurized flow of breathable gas to maintain adequate lung volume, and at the second pressure range pressure through the airway of the subject is reduced to facilitate exhalation of carbon dioxide from the subjects lungs and facilitate tidal ventilation.

The control of the pressure generator includes, effectuating delivery of the pressurized flow of breathable gas to the airway of the subject with the first pressure range at the beginning time of a time interval, effectuating adjustment of the pressurized flow from the first pressure range to the second pressure range responsive to a detection by the synchronization module of a start of a first expiratory flow phase in the time interval or by a predetermined set time period, effectuating maintenance of delivery of the pressurized flow of breathable gas at the second pressure range over the expiratory flow phase; and effectuating maintenance of delivery of the pressurized flow of breathable gas at the first pressure range responsive to a detection by the synchronization module of the start of inspiration or by a predetermined set time period following the first expiratory flow phase. Furthermore, the pressurized flow of breathable gas will be maintained at the first pressure range over all expiratory and inspiratory flows following the first expiratory flow phase until the end time of the time interval.

Yet another aspect of the present disclosure relates to a method for delivering pressure control ventilation configured to provide airway pressure release ventilation synchronous with a breathing subject that includes a pressure generator configured to generate pressurized flow of breathable gas to a subject, a conduit for communicating pressurized flow from the pressure generator to a subject, an interface appliance to communicate the pressurized flow to the airway of the subject, one or more sensors configured to generate output signals conveying information related to one or more gas parameters of the pressurized flow, one or more processors configured to execute computer modules, a power source, a user interface, and electronic storage.

The method comprises generating the pressurized flow of breathable gas with the pressure generator, communicating the pressurized flow of breathable gas to the airway of the subject with the interface appliance, generating output signals conveying information related to one or more gas parameters of the pressurized flow of breathable gas with the one or more sensors, executing computer program modules on the processor, wherein the computer program module detect inspiratory and expiratory flow phases of the breathing subject including detecting starts and ends of the inspiratory and expiratory flow phases of the breathing subject, defining time intervals for providing periodic airway pressure release ventilation including defining beginning times and end times of the time intervals, and controlling the pressure generator to deliver pressurized flow of breathable gas with a pressure that fluctuates between pressure ranges.

Controlling the pressure generator includes controlling the pressure generator to deliver pressurized flow of breathable gas with a pressure that fluctuates between first and second pressure ranges such that at the first pressure range the lungs of the subject are supported by the pressurized flow of breathable gas to maintain adequate lung volume, and at the second pressure range the pressure through the airway of the subject is reduced to facilitate exhalation of carbon dioxide from the subjects lungs and encourage tidal ventilation, effectuating delivery of the pressurized flow of breathable gas to the airway of the subject with the first pressure range at the beginning time of a time interval, effectuating adjustment of the pressurized flow from the first pressure range to the second pressure range responsive to a detection of a start of a first expiratory flow phase in the time interval, effectuating maintenance of delivery of the pressurized flow of breathable gas at the second pressure range over the first expiratory flow phase, and effectuating maintenance of delivery of the pressurized flow of breathable gas at the first pressure range with the option of a programmable pressure support during the inspiratory flow phase following the first expiratory flow phase, and maintaining pressure at the first pressure range over all other expiratory flow phases following the first expiratory flow phase until the start of a new time interval.

Still another aspect of present disclosure relates to a pressure control ventilation system configured to provide airway pressure release ventilation synchronous with a breathing subject, the pressure support system comprising means for generating the pressurized flow of breathable gas, means for communicating the pressurized flow of breathable gas to the airway of the subject, means for generating output signals conveying information related to one or more gas parameters of the pressurized flow of breathable gas, means for executing computer program modules, means for detecting inspiratory and expiratory flow phases of the breathing subject including detecting starts and ends of the inspiratory and expiratory flow phases of the breathing subject, means for defining time intervals for providing periodic airway pressure release ventilation including defining beginning times and end times of the time intervals, and means for controlling the pressure generator to deliver pressurized flow of breathable gas with a pressure that fluctuates between pressure ranges.

The means for controlling the pressure generator includes means for controlling the pressure generator to deliver pressurized flow of breathable gas with a pressure that fluctuates between first and second pressure ranges such that at the first pressure range the lungs of the subject are supported by the pressurized flow of breathable gas to maintain adequate lung volume, and at the second pressure range pressure through the airway of the subject is reduced to facilitate exhalation of carbon dioxide from the subjects lungs and encourage tidal ventilation, effectuating delivery of the pressurized flow of breathable gas to the airway of the subject with the first pressure range at the beginning time of a time interval, effectuating adjustment of the pressurized flow from the first pressure range to the second pressure range responsive to a detection of a start of a first expiratory flow phase in the time interval, effectuating maintenance of delivery of the pressurized flow of breathable gas at the second pressure range over the expiratory flow phase, and effectuating maintenance of delivery of the pressurized flow of breathable gas at the first pressure range over all other expiratory flow phases following the first expiratory flow phase until the end of the time interval.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
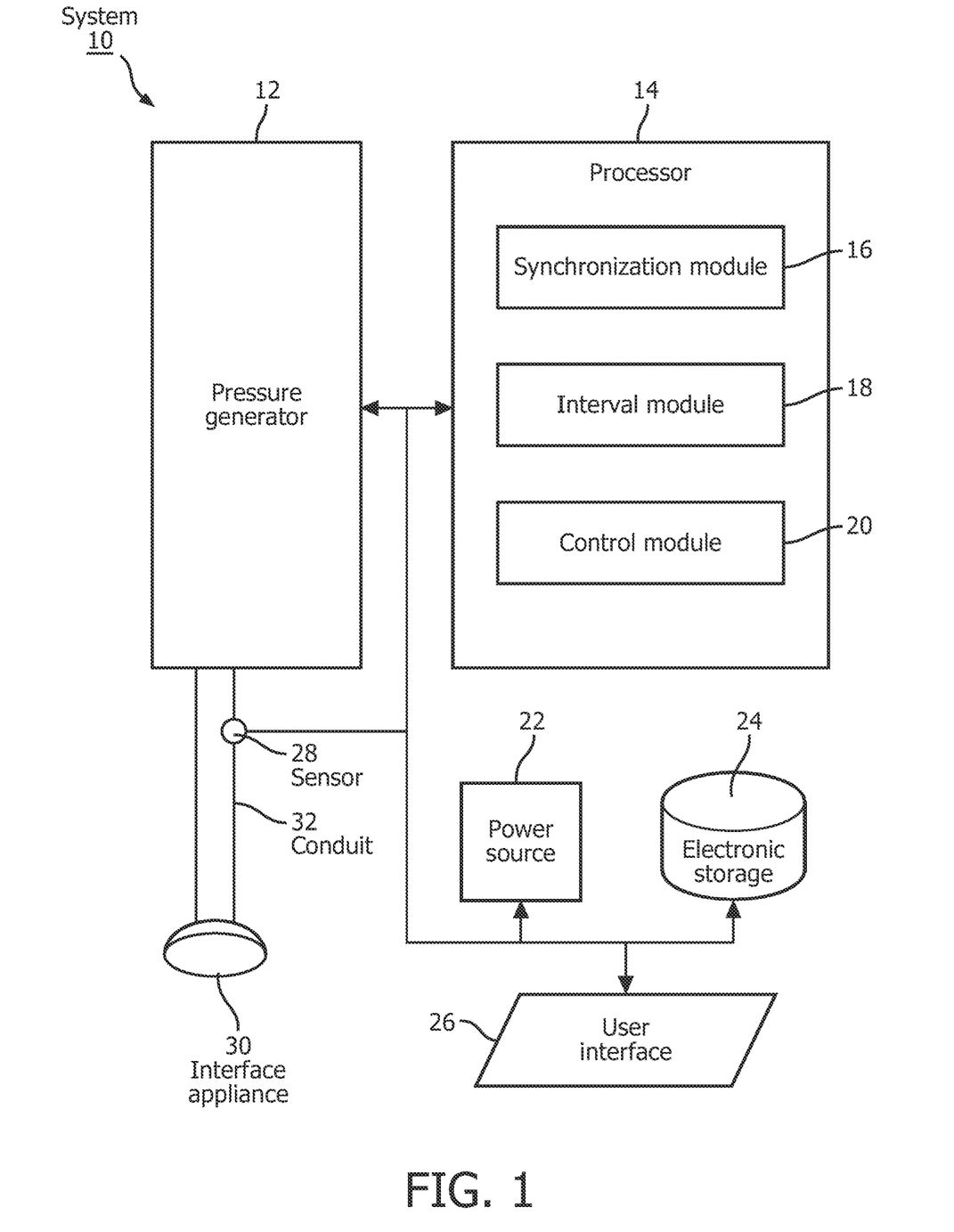
FIG. 1 is a pressure control ventilation system providing airway pressure release ventilation which is synchronous to a patient's breathing pattern that includes a pressure generator configured to generate pressurized flow of breathable gas to a subject, a conduit for communicating pressurized flow from the pressure generator to a subject, an interface appliance to communicate the pressurized flow to the airway of the subject, one or more sensors configured to generate output signals conveying information related to one or more gas parameters of the pressurized flow, one or more processors configured to execute computer modules, a power source, a user interface, and electronic storage.

FIG. 1 schematically illustrates an exemplary embodiment of a pressure control ventilation system 10 configured to provide periodic airway pressure release ventilation synchronous to a subject's breathing pattern. Pressure control ventilation system 10 may be configured to provide the pressure support and ventilation in the form of a pressurized flow of breathable gas that is delivered to the airway of the subject. Pressure control ventilation system 10 may be configured to deliver pressurized flow of breathable gas in multiple pressure ranges. Pressure control ventilation system 10 may be configured to allow subjects to breathe spontaneously during delivery of the pressurized flow of breathable gas at a first pressure range. Pressure control ventilation system 10 may be configured to provide pressure release in the form of delivery of pressurized flow of breathable gas at a second pressure range, wherein the second pressure range is lower than the first pressure range.

The pressure release provided by delivery of pressurized flow of breathable gas at the second pressure range may facilitate the exhalation of carbon dioxide from the subjects' airway at periodic intervals, while delivery of pressurized flow of breathable gas at the first pressure range may improve oxygenation through greater alveolar recruitment. The pressure level being delivered within the first pressure range may be varied to a relatively higher pressure level to provide additional pressure support in the first pressure range during inspiratory flow phases. The pressure level being delivered within the first pressure range may be varied to a relatively lower pressure level to provide pressure relief in the first pressure range during expiratory flow phases.

The present disclosure contemplates that pressure control ventilation system 10 may be used to treat symptoms and/or conditions related to Acute Respiratory Distress Syndrome, Acute Lung Injury, and other forms of respiratory failure or insufficiency, and/or other uses. The other uses may include treatment of central or obstructive sleep apnea, Obesity Hypoventilation Syndrome and related forms of chronic hypoventilation, and/or other uses.

In some embodiments, pressure control ventilation system 10 comprises one or more of a pressure generator 12, one or more processors 14, a power source 22, electronic storage 24, a user interface 26, one or more sensors 28, and/or other components.

Pressure generator 12 is configured to generate a pressurized flow of breathable gas for delivery to the airway of a subject. Pressure generator 12 may include a conduit 32 providing a flow path for delivering the breathable gas to the subject. Conduit 32 may comprise one or more of a flexible conduit, sealed tubing, and/or other component suitable for delivery of pressurized breathable gas. Conduit 32 may be integrally connected to an interface appliance 30. Interface appliance 30 may comprise one or more of a nasal mask, nasal cannula, a full face mask, a nasal pillow mask, a hybrid mask, an oral mask, a total face mask, an endotracheal tube, and/or other invasive and/or non-invasive interface appliance configured to communicate a flow of gas to the airway of a subject. In some embodiments, interface appliance 30 may be removably coupled to conduit 32. Interface appliance 30 may be removed for cleaning and/or for other purposes.

Pressure generator 12 generates pressurized flow of breathable gas according to one or more parameters of the flow of gas (e.g., flow rate, pressure, volume, temperature, gas composition, etc.) for therapeutic purposes, and/or for other purposes. By way of a non-limiting example, pressure generator 12 may be configured to generate pressurized flow at a flow rate and/or pressure of the flow of gas to provide pressure support and/or pressure release ventilation to the airway of a subject.

Pressure generator 12 may receive a flow of gas from a gas source, such as the ambient atmosphere, and elevates the pressure of that gas for delivery to the airway of a subject at a pressurized flow. In some embodiments, pressure generator 12 may receive a flow of gas from a gas source through an inlet port (not shown). Pressure generator 12 may be any device, such as, for example, a pump, blower, piston, or bellows, that is capable of elevating the pressure of the received gas for delivery to a subject. Pressure generator 12 may comprise one or more valves for adjusting the delivery of the pressure/flow of gas. The present disclosure also contemplates controlling the operating speed of the blower, either alone or in combination with such valves, to control the pressure/flow of gas provided to the subject.

In some embodiments, pressure generator 12 is configured to supply a pressurized flow of breathable gas at a first pressure range of about 0 to 50 cm H20. In some embodiments, pressure generator 12 may be configured to supply a pressurized flow of breathable gas at a second pressure range of about 0 to 30 cm H20. In some embodiments, pressure generator 14 may be configured to supply a pressurized flow of breathable gas at other pressures and/or pressure ranges.

One or more sensors 28 are configured to generate output signals conveying information related to one or more parameters of the gas within pressure control ventilation system 10. The one or more parameters of the gas within pressure control ventilation system 10 may comprise gas parameters related to the pressurized flow of breathable gas generated by pressure generator 12, breathing parameters related to respiration of the subject employing pressure control ventilation system 10, and/or other parameters. Sensors 28 may comprise one or more sensors that measure such parameters directly (e.g., through fluid communication with the flow of gas in interface appliance 30, and/or conduit 32). Sensors 28 may comprise one or more sensors that generate surrogate output signals related to the one or more parameters indirectly. For example, sensors 28 may comprise one or more sensors configured to generate an output based on an operating parameter of pressure generator 12 (e.g., patient flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of a subject may comprise a tidal volume, respiratory flow phase (e.g., inspiratory flow phases, expiratory flow phases, etc.), a timing (e.g., start and/or end of inspiratory flow phases, start and/or end of expiratory flow phases, etc.), a respiration rate, a duration (e.g., of inspiratory flow phases, of expiratory flow phases, of a single breathing cycle, etc.), respiration frequency, and/or other breathing parameters.

Although sensors 28 are illustrated at a single location in pressure control ventilation system 10, this is not intended to be limiting. Sensors 28 may comprise sensors disposed in a plurality of locations, such as for example, at various locations within (or in communication with) conduit 32, within pressure generator 12, within (or in communication with) interface appliance 30, and/or other locations.

Processor 14 is configured to provide information processing capabilities in pressure control ventilation system 10. As such, processor 14 may comprise one or more of a digital processor, an analog processor, a digital circuit designed to process information, an analog circuit designed to process information, a state machine, and/or other mechanisms for electronically processing information. Although processor 14 is shown in FIG. 1 as a single entity, this is for illustrative purposes only. In some implementations, processor 14 may comprise a plurality of processing units. These processing units may be physically located within the same device (e.g., pressure generator 12), or processor 14 may represent processing functionality of a plurality of devices operating in coordination.

As shown in FIG. 1, processor 14 is configured to execute one or more computer program modules. The one or more computer program modules may comprise one or more of a synchronization module 16, an interval module 18, a control module 20, and/or other modules. Processor 14 may be configured to execute modules 16, 18, and/or 20 by software; hardware; firmware; some combination of software, hardware, and/or firmware; and/or other mechanisms for configuring processing capabilities on processor 14.

It should be appreciated that although modules 16, 18, and 20 are illustrated in FIG. 1 as being co-located within a single processing unit, in implementations in which processor 14 comprises multiple processing units, one or more of modules 16, 18, and/or 20 may be located remotely from the other modules. The description of the functionality provided by the different modules 16, 18, and/or 20 described below is for illustrative purposes, and is not intended to be limiting, as any of modules 16, 18, and/or 20 may provide more or less functionality than is described. For example, one or more of modules 16, 18, and/or 20 may be eliminated, and some or all of its functionality may be provided by other modules 16, 18, and/or 20. As another example, processor 14 may be configured to execute one or more additional modules that may perform some or all of the functionality attributed below to one of modules 16, 18, and/or 20.

Synchronization module 16 is configured to detect inspiratory and expiratory flow phases of the respiration cycles of a breathing subject employing pressure control ventilation system 10. The detection may be based on the one or more output signals from the one or more sensors 28 conveying information related to flow rate parameters of the gas within pressure control ventilation system 10.

Figure 2:
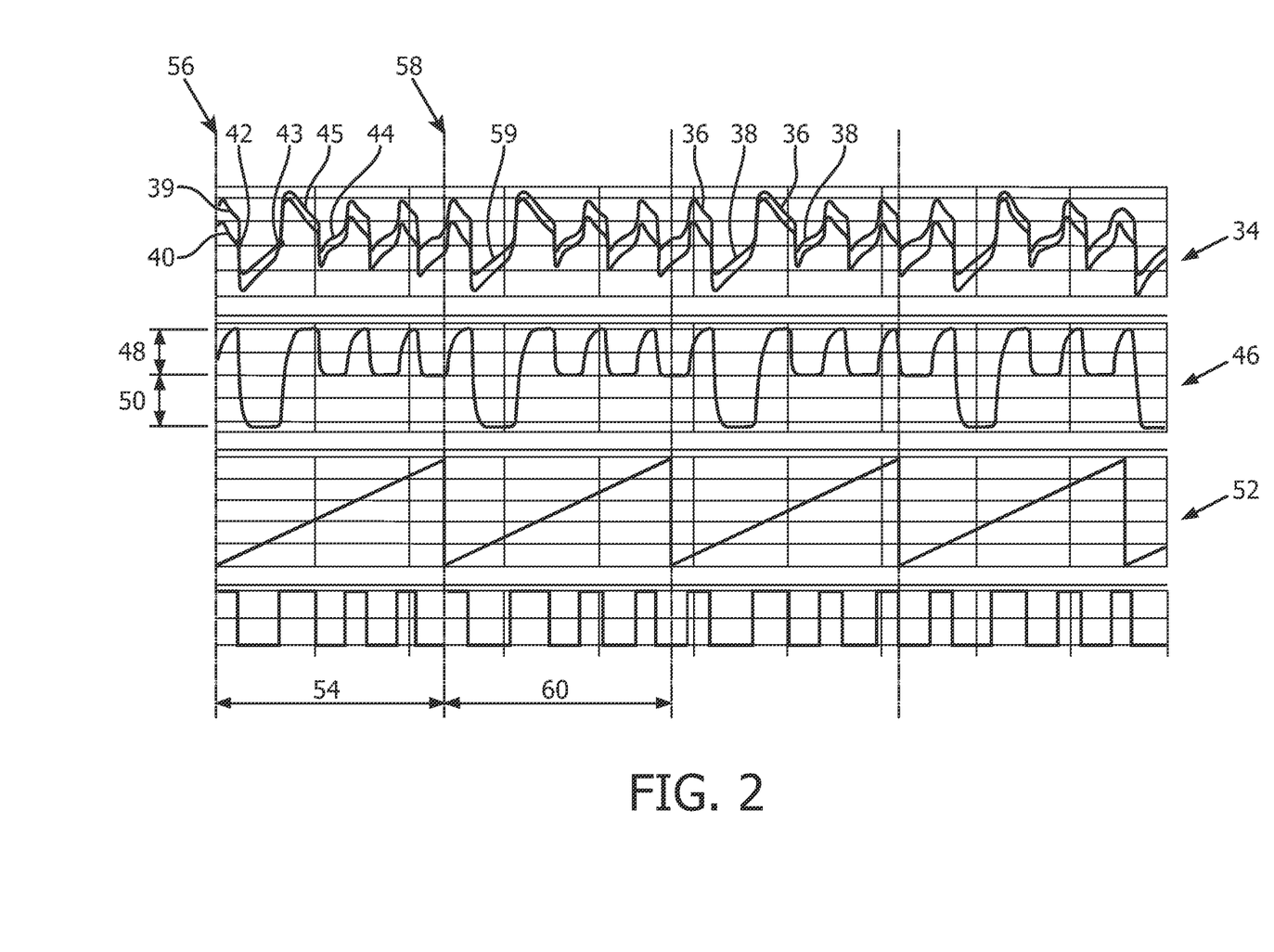
FIG. 2 is an illustration of gas parameters measured over time relating to output signals of the sensors of the pressure control ventilation system.

By way of illustrations, FIG. 2 illustrates plots of gas parameters of the pressurized flow of breathable gas over time (e.g., represented by output signals of one or more sensors). Plot 34 provides a graphical representation of flow rate. In plot 34, the changing respiratory flow rate of the pressurized flow of breathable gas illustrates inspiratory flow phases (e.g., peaks 36 representing inhalation) when flow is positive relative to zero or baseline, and troughs 38 which represent expiratory flow phases (e.g., exhalation) when flow is negative relative to zero or baseline. Transitions between inspiratory flow phases and expiratory flow phases may be determined by the transition or an anticipated transition based on flow trajectory between troughs 38 and peaks 36 as shown graphically in plot 34. Plot 46 provides a graphical representation of the pressure of the pressurized flow of breathable gas generated by pressure generator 12 (e.g., represented by output signals of one or more sensors).

Returning to FIG. 1, synchronization module 16 is configured to detect starts and ends of inspiratory flow phases (e.g., peaks 36 as shown in FIG. 2) and expiratory flow phases (e.g., troughs 38 as shown in FIG. 2). For example, in FIG. 2, a first expiratory flow phase 40 is shown in plot 34. First expiratory flow phase 40 includes a start 42 which occurs at the transition between a first inspiratory flow phase 39 (e.g., temporally first flow phase within the time interval and immediately preceding the first expiratory flow phase 40) and the first expiratory flow phase 40.

In plot 34, the end of the first expiratory flow phase 40 may be indicated by a start 43 of a second inspiratory flow phase 45 immediately following the first expiratory flow phase 40. The start 43 of second inspiratory flow phase 45 indicates the end of first expiratory flow phase 40. In addition, a second expiratory flow phase 44 may also be indicated as the trough immediately following second inspiratory flow phase 45. Second expiratory flow phase 44, does not produce and airway release as during first expiratory phase 40, because interval 54 has yet to expire.

It is noted that although detailed descriptions of start 42 of first expiratory flow phase 40 and start 43 of second inspiratory flow phase 45 are provided, it is to be understood that starts and ends of any and all inspiratory and expiratory flow phases of a respiration cycle of a breathing subject, including those not shown directly in FIG. 2, can be determined from plot 34. As such it is to be understood that detection of starts and ends may be carried out longer or shorter than the time periods depicted by the plots shown in FIG. 2.

It is to be understood for convention in this disclosure, that transitions between inspiratory flow phases (e.g., peaks 36) and expiratory flow phases (e.g., troughs 38) includes both the flow rate measurements representing the end of the inspiratory flow phase and the start of the expiratory flow phase. Therefor the term "end of the inspiratory flow phase" essentially refers to the same flow rate measurements as the term "start of the expiratory flow phase" which immediately follows the inspiratory flow phase. Further it is to be understood that transitions between expiratory flow phases (e.g., troughs 38) and inspiratory flow phases (e.g., peaks 36) includes both the flow rate measurement representing the end of the expiratory flow phase and the start of the inspiratory flow phase. Therefor the term "end of the expiratory flow phase" refers generally to the same flow rate measurements as the term "start of the inspiratory flow phase" which immediately follows the expiratory flow phase.

Returning to FIG. 1, interval module 18 is configured to define time intervals for which pressure control ventilation system 10 provides periodic airway pressure release ventilation. Individual time intervals may encompass one occurrence of airway pressure release ventilation. Individual time intervals may encompass more than one occurrence of airway pressure release ventilation. Time intervals may include beginning times and end times. Time intervals may be defined by user selection through user interface 26 of pressure control ventilation system 10. The user may be the subject, a health care professional, and/or other user. Time intervals may be predetermined by pressure control ventilation system 10. For example time intervals can be set to 15 seconds (or other amount). Time intervals may be dynamically defined by the particular breathing patterns of a subject. For example, intervals may be defined by the average amount of time it takes for a subject to complete four (or other amount) of inspiratory and expiratory flow phases (e.g., breaths).

By way of illustrations, FIG. 2 illustrates plot 52 providing a graphical representation of time intervals. Plot 52 depicts a first time interval 54, a second time interval 60, and/or more and/or less time intervals in which periodic airway pressure release ventilation is provided. In plot 52, the beginning 56 and end 58 of first time interval 54 are temporally indicated. The end 58 of first time interval 54 is defined as the start of second time interval 60.

Flow phases (e.g., peaks 36 and troughs 38 in plot 34) may be temporally defined with respect to time intervals. Flow phases may be designated as temporally first, second, third, etc., flow phases with respect to the beginning and end times of the time intervals. For example, in plot 34 of FIG. 2, first expiratory flow phase 40 is the temporally first expiratory flow phase within first time interval 54 with respect to beginning time 56. Second expiratory flow phase 44 is the temporally second expiratory flow phase with respect to first time interval 54, and so forth. Subsequent expiratory flow phases following first expiratory flow phase 40 may be designated as temporally first expiratory flow phases due to the relationship of the start of a particular expiratory flow phase (e.g., transition from peak 36 to trough 38) with respect a start of a time interval. For example, fifth expiratory flow phase 59 (e.g., the fifth trough 38 when counting left to right) is the temporally first expiratory flow phase with respect to second time interval 60.

In FIG. 1, control module 20 is configured to effectuate delivery and/or adjustment and/or maintenance of a pressure and/or pressure range of pressurized flow of breathable air generated by pressure generator 14 in a variety of ways. Control module 20 is configured to control pressure generator 12 to deliver pressurized flow of breathable gas with a pressure that fluctuates between particular pressure levels and/or pressure ranges. Control module 20 may be configured to effectuate delivery of the pressurized flow of breathable gas to the airway of the subject at an initial pressure level and/or pressure range at the beginning of the time intervals (e.g., at the beginning times or toward the beginning).

Control module 20 may be configured to effectuate adjustment of the pressurized flow from the initial pressure and/or or pressure range to an adjusted pressure and/or pressure range responsive to a detection by synchronization module 16 of a start of a temporally first (and/or second, third, fourth, etc.) expiratory flow phase within the time intervals, and/or other detection by synchronization module 16. Control module 20 may be configured to effectuate maintenance of delivery of the pressurized flow of breathable gas at the adjusted pressure and/or pressure range over the duration of the temporally first (and/or second, third, fourth, etc.) expiratory flow phase, and/or other time duration.

Control module 20 may be configured to effectuate adjustment of the pressurized flow from the adjusted pressure and/or pressure range back to the initial pressure level and/or pressure range, and/or other pressure level and/or pressure range, after the expiration of the duration of the temporally first (and/or second, third, fourth, etc.) expiratory flow phase, and/or other time duration. Control module 20 may be configured to effectuate maintenance of delivery of the pressurized flow of breathable gas at the initial pressure and/or pressure range, and/or other pressure and/or pressure range, over subsequent expiratory flow phases following the temporally first (and/or second, third, fourth, etc.) expiratory flow phase at least until the expiration of the time interval.

Control module 20 is configured to control pressure generator 12 to deliver pressurized flow of breathable gas at a first pressure range (e.g., first pressure range 48 in plot 46 of FIG. 2). Delivery of the pressurized flow of breathable gas allows subjects to breathe spontaneously. At the first pressure range, the lungs of the subject are supported by the pressurized flow of breathable gas to maintain adequate lung volume. Delivery of pressurized flow of breathable gas by pressure generator 12 at the first pressure range may improve oxygenation through greater alveolar recruitment.

Control module 20 is configured to control pressure generator 12 to deliver pressurized flow of breathable gas at a second pressure range (e.g., second pressure range 50 shown in plot 46 of FIG. 2) which facilitates periodic exhalation of carbon dioxide from the subjects' airway at periodic intervals. The second pressure range may be lower than first pressure range. At the second pressure range, pressure of the pressurized flow generated by pressure generator 12 through the airway of the subject is reduced to facilitate exhalation of carbon dioxide from the subject's lungs. The frequency at which control module 20 effectuates delivery of pressurized flow of breathable gas at the second pressure range may be based on detections of any one of temporally first, second, third, fourth, etc. expiratory flow phase within the time intervals.

Figure 3:
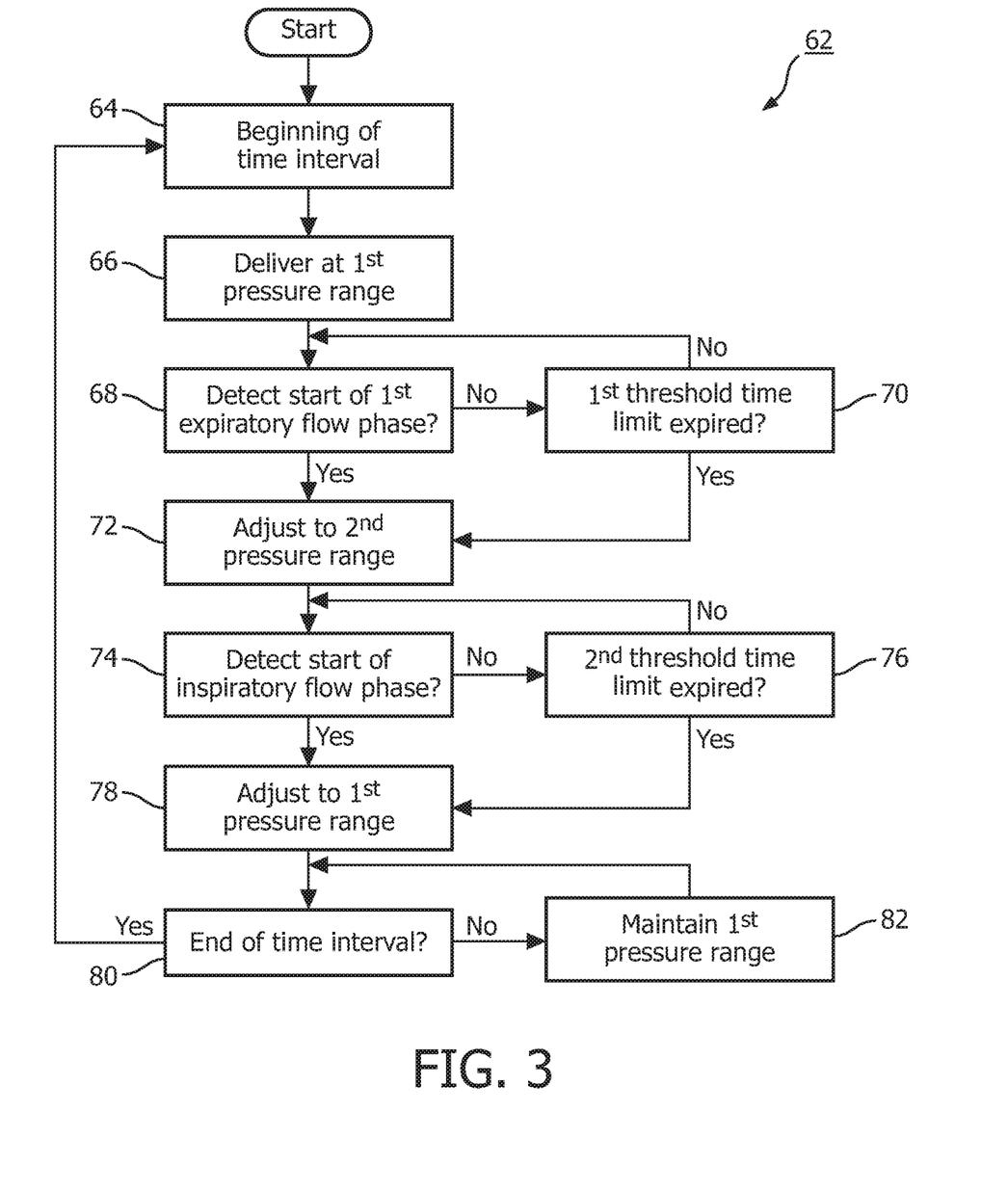
FIG. 3 is a method for controlling the pressure generator of the pressure control ventilation system.

By way of illustration, FIG. 3 depicts exemplary, non-limiting method 62 showing operations of control module 20 of FIG. 1 in controlling pressure generator 12 of FIG. 1 to deliver the pressurized flow of breathable gas so that pressure fluctuates between the first pressure range and the second pressure range. Operations 64 and 66 perform effectuating delivery of the pressurized flow of breathable gas to the airway of the subject at an initial pressure and/or pressure range at the beginning times of the time intervals. Operations 68 and 72 perform adjustment of the pressurized flow from an initial pressure and/or pressure range to an adjusted pressure and/or pressure range responsive to a detection (e.g., by synchronization module 16 of FIG. 1) of a start of a temporally first (and/or second, third, fourth etc.) expiratory flow phase within the time intervals, and/or other detection. Absent a detection of the start of a temporally first (and/or second, third, fourth etc.) expiratory flow phase within time intervals, at operation 70, adjustment of the pressurized flow from the initial pressure and/or pressure range to the adjusted pressure and/or pressure range is performed responsive to a detection of an expiration of a first threshold time limit following the beginning of the time interval.

By way of further illustration, returning to FIG. 2, plot 46 depicts the delivery of the pressurized flow of breathable gas to the airway of the subject at first pressure range 48 at the beginning time 56 of first time interval 54. Adjustment of the pressurized flow from the first pressure range 48 to the second pressure range 50 is depicted responsive to a detection of start 42 of first expiratory flow phase 40 in the first time interval 54 (the first expiratory flow phase 40 being the temporally first expiratory flow phase in first time interval 54). Absent a detection (e.g., by synchronization module 16 of FIG. 1) of start 42 of first expiratory flow phase 40 (e.g., temporally first expiratory flow phase within first time interval 54), adjustment of the pressurized flow from the first pressure range 48 to the second pressure range 50 is responsive to a detection of an expiration of a first threshold time limit following beginning 56 of first time interval 54.

First threshold time limit may be defined by user selection (e.g., through user interface 26 of pressure control ventilation system 10 in FIG. 1). The user may be the subject, a health care professional, and/or other user. First threshold time limit may be predetermined. For example threshold time limit may be set to 2 seconds (or other amount). First threshold time limit may be dynamically defined by the particular breathing patterns of a subject. For example, first threshold time limit may be defined by the average amount of time it takes for the subject to complete inspiratory flow phases (e.g., inhalations).

Returning to FIG. 3, at an operation 74, maintenance of delivery of the pressurized flow of breathable gas at the adjusted pressure level and/or pressure range is performed over the duration of the temporally first (and/or second, third, fourth etc.) expiratory flow phase, and/or other time duration. The duration of the temporally first (and/or second, third, fourth etc.) expiratory flow phase may be the time between a detection of the start of the temporally first (and/or second, third, fourth etc.) expiratory flow phase and the start of the inspiratory flow phase immediately following the temporally first (and/or second, third, fourth, etc.) expiratory flow phase within the time interval.

Absent a detection of the start of the inspiratory flow phase immediately following the temporally first (and/or second, third, fourth etc.) expiratory flow phase within the time interval, an operation 76 may perform maintenance of the delivery of the pressurized flow of breathable gas at the adjusted pressure and/or range over a duration of time which is the time between the start of the temporally first (and/or second, third, fourth etc.) expiratory phase and the end of a second threshold time limit following the start of the temporally first (and/or second, third, fourth etc.) expiratory flow phase. At an operation 78 adjustment of the pressurized flow from the adjusted pressure and/or pressure range back to the initial pressure and/or pressure range, and/or other pressure and/or pressure range is performed after the expiration of the duration of the temporally first (and/or second, third, fourth etc.) expiratory flow phase and/or other time duration associated with maintenance of delivery of the pressurized flow of breathable gas at the adjusted pressure and/or pressure range.

For example returning to FIG. 2, maintaining the delivery of the pressurized flow of breathable gas at the second pressure range 50 over the first expiratory flow phase 40 (e.g., temporally first expiratory flow phase within first interval 54) includes maintaining the delivery of the pressurized flow of breathable gas during the time between the start 42 of the first expiratory flow phase 40 and start 43 of second inspiratory flow phase 45 (e.g., the inspiratory flow phase immediately following first expiratory flow phase 40). Absent a detection of the start 43 of second inspiratory flow phase 45, maintenance of delivery of pressurized flow of breathable gas at second pressure range 50 may be performed during the time between the start 42 of the first expiratory flow phase 40 and the end of a second threshold time limit following the start 42 of the first expiratory flow phase 40. Second threshold time limit may be defined by user selection.

The user may be the subject, a health care professional, and/or other user. Second threshold time limit may be predetermined. For example threshold time limit may be set to 3 seconds (or other amount). Second threshold time limit may be dynamically defined by the particular breathing patterns of a subject. For example, second threshold time limit may be defined by the average amount of time it takes for the subject to complete expiratory flow phases (e.g., exhalations). Responsive to the detection of the expiration of the first expiratory flow phase 40 (e.g., detection of the start 43 of second inspiratory flow phase 45), and/or detection of the expiration of the second threshold time limit following the start 42 of first expiratory flow phase 40, adjustment of pressurized flow from second pressure range 50 back to first pressure range 48 is performed.

Returning to FIG. 3, at operations 80 and 82, maintenance of delivery of the pressurized flow of breathable gas at the initial pressure level and/or pressure range, and/or other pressure level and/or pressure range, over subsequent expiratory and inspiratory flow phases following the temporally first (and/or second, third, fourth etc.) expiratory flow phase is performed at least until the expiration of the time interval. For example, returning to FIG. 2, maintenance of deliver of the pressurized flow of breathable gas first pressure range 48 over subsequent expiratory and inspiratory flow phases following the first expiratory flow phase 40 of first time interval 54 is performed at least until the end 58 of first time interval 54. Maintaining the delivery within first pressure level 48 may include, for example, that the pressure level being delivered within first pressure range 48 may be varied to a relatively higher pressure level within first pressure range 48 to provide additional pressure support during inspiratory flow phases following first expiratory flow phase 40. The pressure level being delivered within first pressure range 48 may be varied to a relatively lower pressure level to provide pressure relief in the first pressure range 48 during expiratory flow phases following first expiratory flow phase 40.

Figure 4:
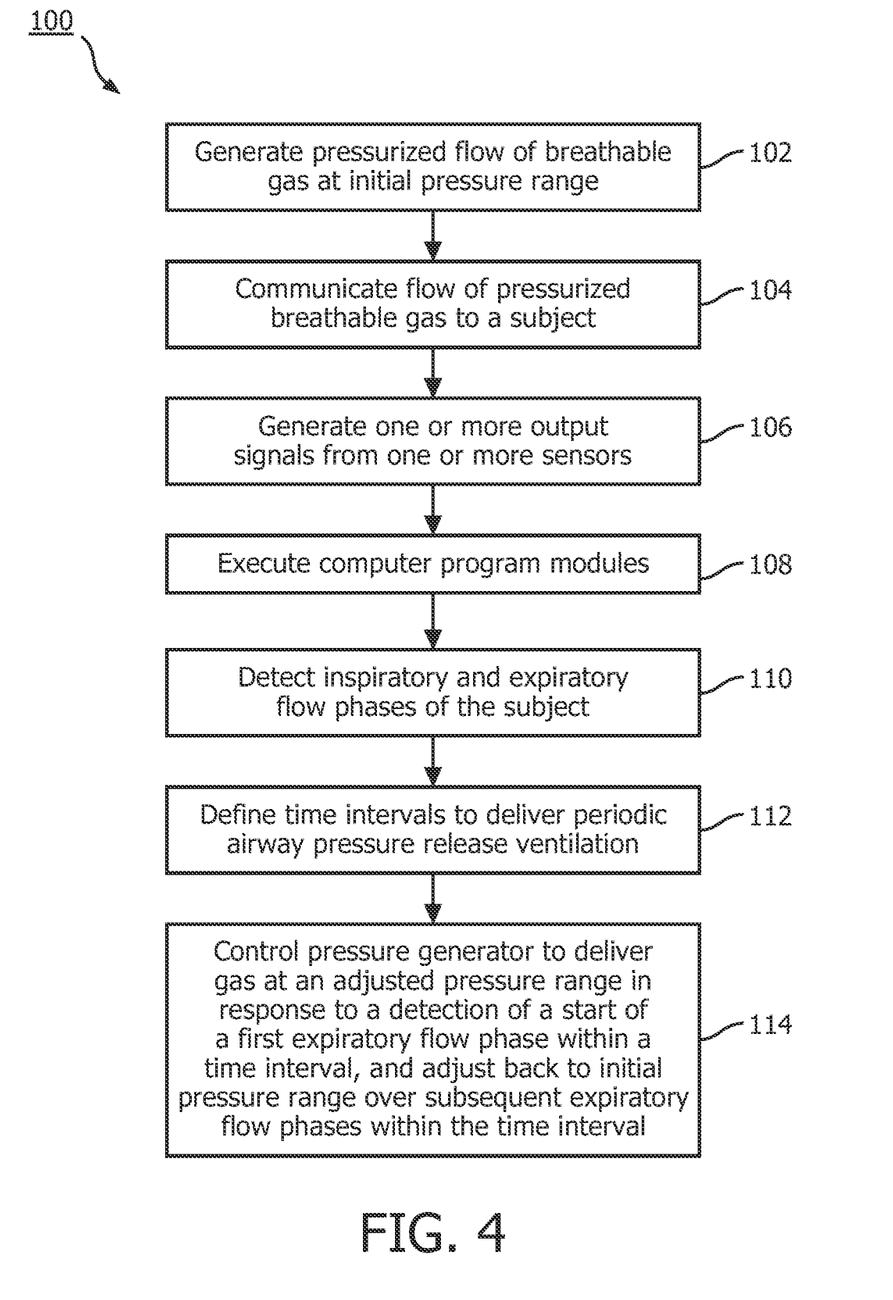
FIG. 4 is a method for delivering pressure control ventilation which provides periodic airway pressure release ventilation which is synchronous to a patient's breathing pattern.

FIG. 4 illustrates a method 100 of delivering pressure control ventilation configured to provide periodic airway pressure release ventilation synchronous to a subject's breathing pattern. The delivery of pressure control ventilation may include a pressure generator configured to generate pressurized flow of breathable gas to a subject, a conduit for communicating pressurized flow from the pressure generator to a subject, an interface appliance to communicate the pressurized flow to the airway of the subject, one or more sensors configured to generate output signals conveying information related to one or more gas parameters of the pressurized flow, one or more processors configured to execute computer modules, a power source, a user interface, electronic storage, and/or other components. The operations of method 100 presented below are intended to be illustrative. In some embodiments, method 100 may be accomplished with one or more additional operations not described, and/or without one or more of the operations discussed. Additionally, the order in which the operations of method 100 are illustrated in FIG. 4 and described below is not intended to be limiting.

In some embodiments, method 100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 100 in response to instructions stored electronically on an electronic storage medium. The one or more processing devices may include one or more devices configured through hardware, firmware, and/or software to be specifically designed for execution of one or more of the operations of method 100.

At an operation 102, the pressurized flow of breathable gas is generated with the pressure generator. In some embodiments, operation 102 is performed by a pressure generator the same as or similar to pressure generator 12 (shown in FIG. 1 and described herein).

At an operation 104, the pressurized flow of breathable gas is communicated to the airway of the subject with the interface appliance. In some embodiments, operation 104 is performed by an interface appliance the same as or similar to interface appliance 30 (shown in FIG. 1 and described herein).

At an operation 106, one or more output signals conveying information related to one or more gas parameters of the pressurized flow of breathable gas are generated with the one or more sensors. In some embodiments, operation 106 is performed by sensors the same as or similar to sensors 28 (shown in FIG. 1 and described herein.)

At an operation 108, one or more program modules are executed by one or more processors. In some embodiments, operation 108 is performed by one or more processors the same as or similar to processor 14 (shown in FIG. 1 and described herein).

At an operation 110, inspiratory and expiratory flow phases of the breathing subject are detected. The detection may include detecting starts and ends of the inspiratory and expiratory flow phases of the breathing subject. The detection may be based in part on the output signals of the one or more sensors from operation 106. In some embodiments, operation 110 is performed by a synchronization module the same as or similar to synchronization module 16 (shown in FIG. 1 and described herein).

At an operation 112, time intervals for providing periodic airway pressure release ventilation are defined. The time intervals may include beginning times and end times. In some embodiments, operation 112 is performed by an interval module the same as or similar to interval module 18 (shown in FIG. 1 and described herein).

At an operation 114, the pressure generator is controlled to deliver pressurized flow of breathable gas with a pressure that fluctuates between pressure ranges. Such control may include controlling the pressure generator to deliver pressurized flow of breathable gas with a pressure that fluctuates between first and second pressure ranges such that at the first pressure range the lungs of the subject are supported by the pressurized flow of breathable gas to prevent collapse of the lungs, and at the second pressure range pressure through the airway of the subject is reduced to facilitate exhalation of carbon dioxide from the subjects lungs. Such control may include, effectuating delivery of the pressurized flow of breathable gas to the airway of the subject with the first pressure range at the beginning time of a first time interval, effectuating adjustment of the pressurized flow from the first pressure range to the second pressure range responsive to a detection by the synchronization module of a start of a temporally first (and/or second, third, fourth, etc.) expiratory flow phase in the first time interval, effectuating maintenance of delivery of the pressurized flow of breathable gas at the second pressure range over the first (and/or second, third, fourth, etc.) expiratory flow phase, and effectuating maintenance of delivery of the pressurized flow of breathable gas at the first pressure range over subsequent expiratory flow phases following the first (and/or second, third, fourth, etc.) expiratory flow phase, that start in the first time interval. In some embodiments, operation 114 is performed by a control module the same as or similar to control module 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure control ventilation system configured to provide airway pressure release ventilation synchronous with a breathing subject, the pressure support system comprising:
    (a) a pressure generator configured to generate a pressurized flow of breathable gas;
    (b) one or more sensors configured to generate output signals conveying information related to one or more gas parameters of the pressurized flow of breathable gas; and
    (c) one or more processors configured to execute computer program modules, the computer program modules comprising:
        (1) a synchronization module configured to detect inspiratory and expiratory flow phases of the breathing subject, including detecting starts and ends of the inspiratory and expiratory flow phases of the breathing subject, the detection based in part on the output signals of the one or more sensors;
        (2) an interval module configured to:
            (i) determine amounts of time the subject takes to complete inspiratory flow phases and expiratory flow phases, the amounts of time determined during ventilation based in part on the output signals of the one or more sensors; and
            (ii) define time intervals, the time intervals having start times and end times, the time intervals being determined based on the amounts of time the subject takes to complete inspiratory flow phases and expiratory flow phases during ventilation, the time intervals including a first time interval; and
        (3) a control module configured to control the pressure generator to deliver the pressurized flow of breathable gas with a pressure that fluctuates between first and second pressure ranges, the first pressure range being higher than the second pressure range, such that delivering the pressurized flow of breathable gas at the second pressure range reduces a gas pressure in the airway of the subject relative to the gas pressure when delivering the pressurized flow of breathable gas at the first pressure range, wherein such control of the pressure generator includes:
            (i) providing the flow of breathable gas to the airway of the subject within the first pressure range over the first time interval, wherein the first time interval spans a plurality of respiratory cycles, and
            (ii) providing the flow of breathable gas to the airway of the subject at the second pressure range responsive to the following conditions being detected:
                (a) the first time interval has elapsed, and
                (b) the synchronization module has detected a start of an expiratory flow phase.

2. The system of claim 1, wherein the control module is further configured to provide the flow of breathable gas to the airway of the subject at the first pressure range responsive to the synchronization module detecting an end of the expiratory flow phase.

3. The system of claim 1, wherein the control module is further configured such that providing the flow of breathable gas to the airway of the subject within the first pressure range over the first time interval includes adjusting the pressure level of the pressurized flow to different values within the first pressure range during different expiratory flow phases during the first time interval.

4. The system of claim 1, wherein the control module is further configured such that providing the flow of breathable gas to the airway of the subject within the first pressure range over the first time interval includes varying the pressure level of the pressurized flow within the first pressure range to a relatively higher pressure during inspiratory flow phases and to a relatively lower pressure during expiratory flow phases.

5. The system of claim 1, wherein the interval module is configured such that determining the amounts of time the subject takes to complete inspiratory flow phases and expiratory flow phases comprises determining the average amounts of time the subject takes to complete inspiratory flow phases and expiratory flow phases, and the time intervals are determined based on the average amounts of time.

6. A method for controlling a pressure generator to provide airway pressure release ventilation synchronous with a breathing subject, the method being implemented by a ventilation system including the pressure generator, one or more sensors configured to generate output signals conveying information related to one or more gas parameters of a pressurized flow generated by the pressure generator, one or more physical processors configured to execute computer program modules, a power source, a user interface, and electronic storage, the method comprising:
    generating the pressurized flow of breathable gas with the pressure generator;

generating output signals conveying information related to one or more gas parameters of the pressurized flow of breathable gas with the one or more sensors;

executing computer program modules on the processor;

detecting inspiratory and expiratory flow phases of the breathing subject including detecting starts and ends of the inspiratory and expiratory flow phases of the breathing subject;

defining time intervals for providing periodic airway pressure release ventilation, the defining time intervals including:

determining amounts of time the subject takes to complete inspiratory flow phases and expiratory flow phases, the amounts of time determined during ventilation based in part on the output signals of the one or more sensors; and defining beginning times and end times of the time intervals, the time intervals being determined based on the amounts of time the subject takes to complete inspiratory flow phases and expiratory flow phases during ventilation, the time intervals including a first time interval; and controlling the pressure generator to deliver the pressurized flow of breathable gas with a pressure that fluctuates between pressure ranges, including controlling the pressure generator to deliver the pressurized flow of breathable gas with a pressure that fluctuates between first and second pressure ranges, the first pressure range being higher than the second pressure range, such that delivering the pressurized flow of breathable gas at the second pressure range reduces a gas pressure in the airway of the subject relative to delivering the pressurized flow of breathable gas at the first pressure range, wherein controlling the pressure generator comprises:

i) providing the flow of breathable gas to the airway of the subject within the first pressure range over the first time interval, wherein the first time interval spans a plurality of respiratory cycles, and ii) providing the flow of breathable gas to the airway of the subject at the second pressure range responsive to the following conditions being detected:
(a) the first time interval has elapsed, and
(b) a start of an expiratory flow phase has been detected.

7. The method of claim 6, wherein controlling the pressure generator to provide the flow of breathable gas to the airway of the subject at the first pressure range is responsive to detecting an end of the expiratory flow phase.

8. The method of claim 6, wherein providing the flow of breathable gas to the airway of the subject within the first pressure range over the first time interval includes adjusting the flow of breathable gas to different values within the first pressure range during different expiratory flow phases during the first time interval.

9. The method of claim 6, wherein providing the flow of breathable gas to the airway of the subject within the first pressure range over the first time interval includes varying the pressure level of the pressurized flow within the first pressure range to a relatively higher pressure during inspiratory flow phases and to a relatively lower pressure during expiratory flow phases.

10. The method of claim 6, determining the amounts of time the subject takes to complete inspiratory flow phases and expiratory flow phases comprises determining the average amounts of time the subject takes to complete inspiratory flow phases and expiratory flow phases, and the time intervals are determined based on the average amounts of time.

11. A pressure control ventilation system configured to provide airway pressure release ventilation synchronous with a breathing subject, the pressure support system comprising:

means for generating a pressurized flow of breathable gas;

means for communicating the pressurized flow of breathable gas to the airway of the subject;

means for generating output signals conveying information related to one or more gas parameters of the pressurized flow of breathable gas;

means for executing computer program modules;

means for detecting inspiratory and expiratory flow phases of the breathing subject including detecting starts and ends of the inspiratory and expiratory flow phases of the breathing subject;

means for defining time intervals for providing periodic airway pressure release ventilation, defining time intervals including:

determining amounts of time the subject takes to complete inspiratory flow phases and expiratory flow phases, the amounts of time determined during ventilation based in part on the output signals of the one or more sensors; and defining start times and end times of the time intervals, the time intervals being determined based on the amounts of time the subject takes to complete inspiratory flow phases and expiratory flow phases during ventilation, the time intervals including a first time; and means for controlling the means for generating the pressurized flow of breathable gas to deliver the pressurized flow of breathable gas with a pressure that fluctuates between pressure ranges, the means for controlling the means for generating the pressurized flow of breathable gas including means for controlling the means for generating the pressurized flow of breathable gas to deliver the pressurized flow of breathable gas with a pressure that fluctuates between first and second pressure ranges, the first pressure range being higher than the second pressure range, wherein the controlling means:

i) provides the flow of breathable gas to the airway of the subject within the first pressure range over a first time interval, wherein the first time interval spans a plurality of respiratory cycles, and ii) provides the flow of breathable gas to the airway of the subject at the second pressure range responsive to the following conditions being detected:
(a) the first time interval has elapsed, and
(b) a start of an expiratory flow phase has been detected.

12. The system of claim 11, wherein the means for controlling the means for generating the pressurized flow of breathable gas is further configured to provide the flow of breathable gas to the airway of the subject at the first pressure range responsive to detection of an end of the expiratory flow phase.

13. The system of claim 11, wherein the means for controlling the means for generating the pressurized flow of breathable gas provides the flow of breathable gas to the airway of the subject within the first pressure range over the first time interval such that the pressure level is adjusted to different values within the first pressure range during different expiratory flow phases during the first time interval.

14. The system of claim 11, wherein the means for controlling the means for generating the pressurized flow of breathable gas provides the flow of breathable gas to the airway of the subject within the first pressure range over the first time interval such that the pressure level varies within the first pressure range to a relatively higher pressure during inspiratory flow phases and to a relatively lower pressure during expiratory flow phases.

15. The system of claim 11, wherein the means for defining time intervals are configured such that determining the amounts of time the subject takes to complete inspiratory flow phases and expiratory flow phases comprises determining the average amounts of time the subject takes to complete inspiratory flow phases and expiratory flow phases, and the time intervals are determined based on the average amounts of time.

\* \* \* \* \*